United States Patent [19]

Weissman

[11] Patent Number: 4,604,060
[45] Date of Patent: Aug. 5, 1986

[54] DENTAL POST SYSTEM
[75] Inventor: Bernard Weissman, New York, N.Y.
[73] Assignee: Ipco Corporation, White Plains, N.Y.
[21] Appl. No.: 733,958
[22] Filed: May 14, 1985
[51] Int. Cl.⁴ ................................................ A61C 5/08
[52] U.S. Cl. .................................................... 433/221
[58] Field of Search ................................ 433/220, 221

[56] References Cited
U.S. PATENT DOCUMENTS

| | | | |
|---|---|---|---|
| 688,661 | 12/1901 | Miller | 433/220 |
| 3,083,461 | 4/1963 | Hirschhorn | 437/219 |
| 4,479,783 | 10/1984 | Weissman | 433/220 |

Primary Examiner—Robert Peshock
Attorney, Agent, or Firm—Goodman & Teitelbaum

[57] ABSTRACT

A dental post system for use in the formation and retention of a dental restoration on a tooth stub. The system includes a dental post having an elongated cylindrical pin with a lower anchoring portion which is secured into a prepared bore in the tooth stub, and an upper end portion which projects from the tooth stub and is secured in a metallic core upon which the restoration is fabricated. An interlock arrangement coacts with the upper end portion to provide permanent securement of the metallic core on the cylindrical pin. The interlock arrangement prevents axial lift off of the metallic core from the dental post as well as preventing rotational displacement between the metallic core and the dental post. A core pattern is used to form the metallic core, where the core pattern can be fabricated from a preformed plastic core or can be built up directly onto the upper end portion when the dental post is disposed in the bore of the tooth stub.

42 Claims, 37 Drawing Figures

DENTAL POST SYSTEM

BACKGROUND OF THE INVENTION

This invention relates to dental posts, and more particularly to a method and apparatus utilizing a dental post system for the formation and retention of a dental restoration.

Various dental procedures are known which utilize dental posts in the restoration and reinforcement of devitalized dentition. In these procedures, dental posts are initially inserted into a prepared tooth stub. A dental restoration is then built up on the tooth stub. Prior to the building of the restoration, a core is first provided directly on the tooth stub, and it is upon the core that the restoration is fabricated.

In the various methods available, the tooth is first prepared to receive the dental post. The apical section of the canal is sealed with gutta percha. A bore is drilled into the tooth, typically along the canal, to a desired depth. In one known method, referred to as the stainless steel technique, a steel dental post is permanently cemented into the bore with a portion projecting from the tooth stub. A core is built up on the tooth stub encompassing the projecting end of the dental post. The core is formed of amalgom or composite material. The final restoration is then built up around the core.

Although this technique is useful for an economical and quick procedure, the core that is formed is only of amalgom or composite material and cannot provide the superiority of a metallic core, such as a gold core. The reason that the amalgom or composite core is utilized is that this material will adhere to the tooth stub and the projecting end of the dental post, and this core can be easily formed directly in the patient's mouth. Metallic material, on the other hand, would have to be cast and therefore cannot be formed directly in the patient's mouth, and furthermore if cast separately, the metallic material would not adhere directly onto the dental post and tooth stub, where additional cement or adhesive would be required.

In order to provide a metallic core, it is known to use either the direct or indirect technique. In the direct technique, an initial burn-out post is temporarily inserted into the bore formed into the tooth stub with a portion of the post projecting from the stub. Resin is then applied and shaped into a core. The resin together with the temporarily inserted post are then entirely removed from the tooth stub and used as a pattern which is sprued and invested using standard investment casting techniques in order to form a unitary metallic core and metallic post assembly in one piece. Typically, precious or non-precious alloys are utilized in the formation of the metal core and post. The core and post are cast together as a one piece unit, where this one piece core and post unit is reinserted into the channel in the tooth stub and permanently secured in place to form a foundation for the restorative dentistry.

In the indirect technique, again a temporary post is inserted into the tooth stub bore, and an impression is taken of the top of the tooth stub including the projecting portion of the dental post. A master model is then fabricated to form a positive. A suitable negative die is formed from this positive. The unitary core and post pattern is then fabricated using a conventional lost wax method or using self curing resin. From this pattern, through investment casting, a suitable one piece metallic core and post unit is cast. This unit can then be inserted into the tooth stub and permanently secured in place to form a foundation for the restorative dentistry.

In both the direct and indirect method, a temporary crown is usually formed during the time when the unitary metallic post and core unit is being cast. Once the metallic post and crown unit has been formed and inserted into the tooth stub, the suitable restoration can then be fabricated on the metallic core.

While both the direct and indirect methods are extremely useful and provide extremely strong restorations, they require the post and core to be formed as a one piece unit. Thus, the post must be made from the same material as the core, which in most cases is a precious metal, such as gold. Obviously, a stainless steel post would be stronger than a gold post, and a gold core is better than a stainless steel core, however the use of two different metals is not possible with the direct and indirect methods.

Accordingly, it would be superior to provide the best aspects of the various existing techniques. For example, it would be most effective to utilize the aspect of the stainless steel technique which permits the inserted metallic dental post to be permanently placed in the tooth stub bore. It would also be beneficial to provide for a precious metallic core which can be cast without the post, and then permanently secured onto the post. However, thus far, the prior art has not been able to provide for the most beneficial aspects of the existing techniques. In the prior art, the core and post were cast as a unitary structure since there was no suitable method or structure to permanently secure the cast core onto a metallic dental post.

SUMMARY OF THE INVENTION

Accordingly, it is an object of the present invention to provide an improved dental post system which avoids the aforementioned problems of the prior art devices.

A further object of the present invention is to provide an improved dental post system which permits the securement of a metallic cast core directly onto a metal dental post.

Still a further object of the present invention is to provide a dental post system wherein a metallic core can be cast and secured onto an upper end of a dental post, whereby the post can be previously cemented into a bore of a tooth stub, or the post can be cemented into the bore together with the metallic core after the metallic core is secured to the post.

Yet another object of the present invention is to provide a dental post having an interlock arrangement associated with its projecting upper end to retain a cast metallic core in place on the dental post.

Another object of the present invention is to provide a method of forming and retaining a dental restoration onto a tooth stub which provides for the use of a dental post and the casting of a metallic core separate from the post.

Still another object of the present invention is to provide an improved dental post system having a dental post with an interlock arrangement for a preformed plastic core so that the plastic core can be secured onto the dental post, the plastic core being utilized to form a core pattern for the direct casting of a metallic core.

A further object of the present invention is to provide a dental post system for use in the direct casting of a metallic core, and including an interlock arrangement for securing the dental post to the metallic core.

Briefly, in accordance with the present invention, there is provided a dental post system for use in the formation of a dental restoration. The dental post includes an elongated cylindrical pin having a lower anchor portion for secured retention within a cement prepared bore in a tooth stub. An upper end portion of the cylindrical pin projects from the tooth stub and is used for patterning a receiving channel in a direct cast metallic core upon which the restoration is fabricated. An interlock arrangement is provided with at least a portion of the interlock arrangement formed on the upper end portion for defining a mating pattern into the cast metallic core to thereby permit securement of the cast metallic core onto the cylindrical pin. The interlock arrangement prevents both axial lift-off as well as rotational displacement between the metallic core and the dental post.

In an embodiment of the present invention, a preformed plastic core is provided with mating portions to the interlock arrangement. The preformed plastic core is mounted onto the upper end of the dental post and connected to the post through the interlock arrangement. Wax is placed at the interface between the tooth stub and the preformed plastic core. The plastic core can then be contoured to a desired shape. The interlock arrangement is then removed and the preformed plastic core and wax are now utilized in the direct casting of a metallic core. The metallic core is then mounted onto the upper end of the dental post and the interlock arrangement is utilized to permanently secure the metallic core onto the dental post. The metallic core is permanently cemented onto the tooth stub with the dental post being secured in the tooth stub.

In another embodiment of the present invention, after the dental post is inserted into the tooth stub, the interlock arrangement is assembled and impression material is used to form a core pattern onto the tooth stub about the upper end of the dental post and the interlock arrangement. This impression material defines the core pattern which is then used in the casting of the metallic core. Again, the metallic core is mounted onto the dental post, the interlock arrangement is reinserted, and the metallic core is cemented onto the tooth stub with the dental post being secured in the tooth stub.

In either of the above embodiments, the dental post can be initially cemented into the bore of the tooth stub prior to the mounting of the preformed plastic core or the formation of the core pattern, or the dental post can be cemented into the tooth stub before or after the dental post is secured to the metallic core.

The interlock arrangement can take various forms. By way of example, it can be a U-shaped clip member with part of the thickness of the legs being received in opposing grooves straddling the upper end portion of the dental post. The other part of each leg thickness being received in associated mating grooves which are provided in the core, thereby locking the core to the upper end portion of the dental post.

Other types of interlock arrangements can be utilized, such as a crosspin inserted transversely through at least a portion of the dental post and extending outwardly through the core. A tapered lock can be used, including a radially directed key formed at the top of the dental post which is matingly received in a keyway formed in the core. The upper end of the dental post can also be formed with an external thread which is received in a threaded bore formed in the core, including a locking pin which is inserted through a side wall of the core and received within a detent in the dental post. Alternately, in place of the threaded core bore, a threaded nut can be secured on the threaded upper end of the post, and additionally in place of the locking pin, the threaded upper end of the post can be provided with a flat surface with the core bore matingly conforming thereto.

The present invention also contemplates a method for restoring devitalized dentition by initially preparing a tooth stub for receiving a permanent post therein. The lower portion of the dental post will ultimately be permanently cemented into the tooth stub with the upper end portion projecting from the tooth stub. An interlock arrangement is provided on the upper end portion for use in the permanent securement of a metallic core on the dental post. A core pattern is initially formed directly onto the tooth stub using an impression material. The upper end portion and the interlock arrangement are provided for in the core pattern to define mating portions therein. The core pattern is then utilized to cast a metallic core. Alternately, a preformed plastic core can be used to cast the metallic core instead of forming the core pattern, where the plastic core provides for the upper end portion of the dental post and for the interlock arrangement. The metallic core is mounted onto the dental post and interlocked with the dental post. Both the metallic core and the dental post are cemented in place with respect to the tooth stub. The restoration can then be fabricated onto the metallic core.

In utilizing the above method of the present invention, the dental post can be initially cemented in place prior to the formation of the core pattern or the mounting of the performed plastic core, or the dental post can be cemented in place before or after its securement to the metallic core, where both the metallic core and the dental post are cemented in place with respect to the tooth stub.

It is noted, that more than one dental post can be utilized in the formation of a dental restoration.

BRIEF DESCRIPTION OF THE DRAWINGS

With the above and additional objects and advantages in view as will hereinafter appear, this invention comprises the devices, combinations and arrangements of parts hereinafter described, by way of example, and illustrated in the accompanying drawings of the preferred embodiments, in which.

In the various figures of the drawing, like reference characters designate like parts.

DETAILED DESCRIPTION OF THE PREFERRED EMBODIMENTS

Figure 1:
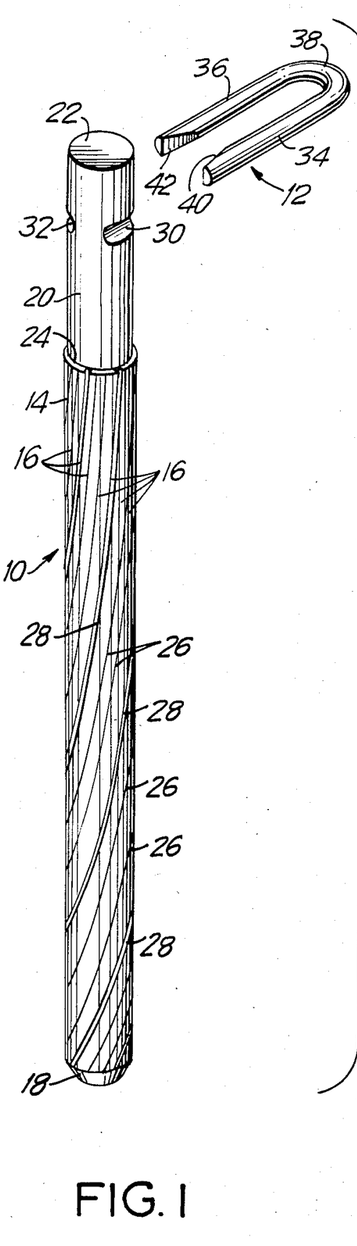
FIG. 1 is an exploded perspective view of a dental post and clip member, in accordance with the present invention.

Referring now to FIG. 1, the dental post system of the present invention is shown to include a dental post shown generally at 10, and a clip member shown generally at 12. The dental post 10 is formed as a cylindrical pin 14 having a plurality of helical flutes 16 formed therein. The lower end 18 of the pin 14 is chamfered. The upper end portion 20 of the pin 14, which can be formed without any flutes, is substantially cylindrical in shape, the top end 22 thereof being substantially flat. A radially extending shoulder 24 separates the fluted lower portion from the upper end portion 20 to define a stop for a core member, as will hereinafter be described. This results in the upper end portion 20 having a slightly reduced diameter than the lower portion of the pin 14.

The fluted post 10 shown is of the type described in more detail in the inventor's U.S. Pat. No. 4,479,783. In general, the flutes 16 are provided with a very large pitch and, as shown, the pitch of each flute is greater than the length of the pin. Because of such a large pitch, a large number of separate individual helices can be provided on the pin 14.

As a result of the multiple flute lines that terminate at the bottom of the post 10, when the lower end 18 is inserted into a prepared tooth bore, there are a plurality of flute lines available for the escape of the air in the bore, and thus the hydrostatic pressure caused during insertion of the post can therefore be reduced as the air escapes along the multi-flute lines, each flute providing a separate venting path. Accordingly, the flutes serve for the assistance in the retention of the post in the bore, and also simultaneously serve as a vent, without the need of any additional vent channel in the post as is required in the prior art.

As noted in FIG. 1, the grooves of the flutes can be formed of different sizes. Specifically, there are two flute sizes shown. A few pairs of smaller grooves 26 are provided, each pair being spaced between the larger grooves 28 on either side thereof.

Although the particular type of cylindrical post heretofore described is one including flutes of different sizes, it should be appreciated that the post could include flutes of a common size, all of which are equally spaced about the periphery of the post.

Additionally, in place of the flutes, a cylindrical post having an external thread could also be utilized, typically of the type described in the inventor's U.S. Pat. No. 4,348,183. In this latter patent, an external spiral thread is provided about the periphery of the dental post, where the post further includes a vent channel vertically extending into the periphery of the post.

At the upper end portion 20 of the dental post 10 shown in FIG. 1, there are provided a pair of opposing horizontal semi-spherical grooves or channels 30, 32 lying along a common plane and extending inwardly into the periphery of the cylindrical pin 14. These grooves 30, 32 are available for partially receiving therein the legs of the clip member 12, as will hereinafter be explained.

The clip member 12 is formed of a continuous cylindrical wire bent into a substantially U-shaped configuration having a pair of opposing legs 34, 36 interconnected by a bight portion 38 therebetween. With the clip member placed so as to straddle the upper end portion 20 of the post 10, the legs 34, 36 are partially received within the opposing grooves 30, 32. The forward ends 40, 42 of the legs 34, 36 are tapered from their distal ends to facilitate the insertion of the legs 34, 36 into the grooves 30, 32.

Figure 2:
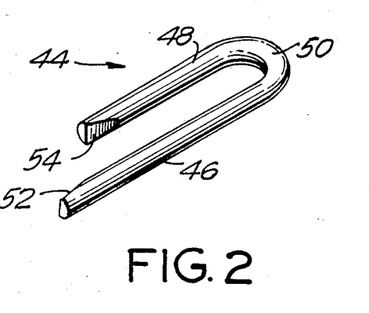
FIG. 2 is a perspective view of another embodiment of the clip member for use with the dental post shown in FIG. 1.

Referring now to FIG. 2, it will be noted that modifications of the clip member can also be provided. Specifically, as shown in FIG. 2, a clip member 44 is formed from a unitary cylindrical wire rod and includes a first leg 46 with an opposing leg 48, wherein the leg 46 is longer than the leg 48. A bight portion 50 interconnects the two legs. With one leg being longer, it is easier to insert the legs into the receiving grooves, where the longer leg acts as a pilot to locate the groove. Again, the distal ends 52, 54 are tapered.

Figure 3:
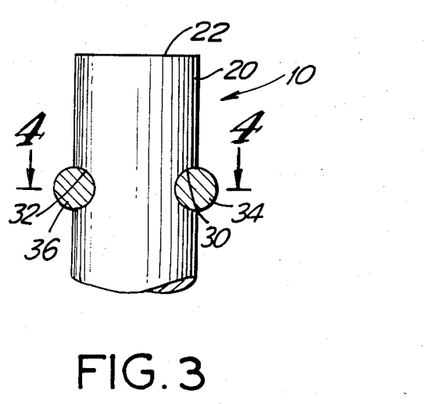
FIG. 3 is an enlarged view of the projecting upper end portion of the dental post shown in FIG. 1, showing a cross section of the clip member straddling the end portion.
Figure 4:
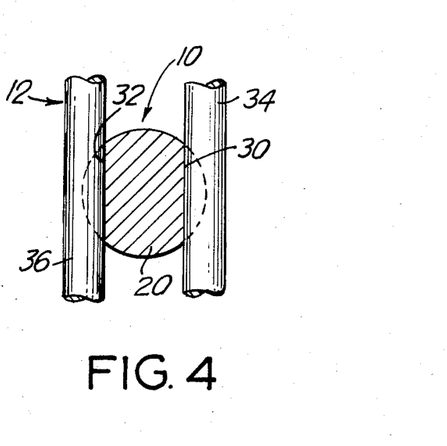
FIG. 4 is a partial sectional view taken along line 4—4 of FIG. 3.
Figure 5:
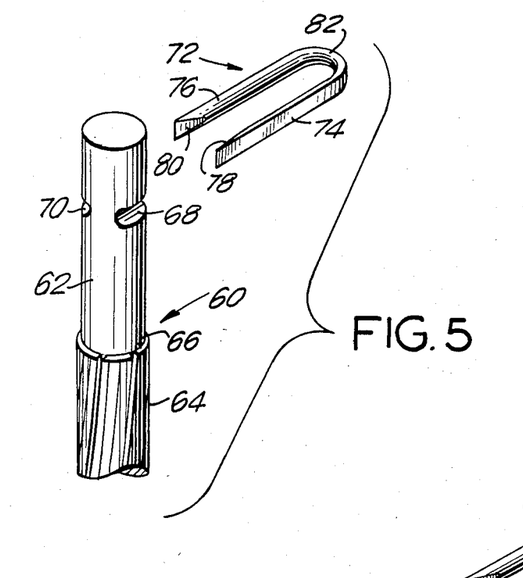
FIG. 5 is an exploded fragmented perspective view of a dental post with a different clip member, in accordance with the present invention.

As shown in FIGS. 3 and 4, the U-shaped clip member 12 is inserted into the grooves 30, 32 to straddle the end portion 20. A portion of the thickness of the cylindrical legs 34, 36 will be received within the grooves, and a portion will project outward of the grooves. As will hereinafter be explained, the portion extending outward of the grooves will mate with a groove pattern within a dental core. In this manner, the thickness of the legs of the U-shaped clip member not received within the pin grooves 30, 32 will be received within mating groove portions provided in the core, whereby the U-syaped clip member serves to lock the core to the dental post, as will hereinafter be described.

In the embodiments shown in FIGS. 1-4, the U-shaped clip member was formed of a substantially circular cross sectional configuration. As will now be described in connection with FIGS. 5-8, similar arrangements can be provided with the U-shaped clip member being formed of half-round stock sections, whereby the outer surface of the clip member is substantially flat.

More particularly, as shown in FIG. 5, there is again provided a dental post formed as a cylindrical pin, shown generally at 60, having an upper end portion 62 and a fluted lower portion 64 separated by a shoulder 66, the structure thus far described being the same as the dental post 10. A pair of opposing grooves 68, 70 are laterally formed into the end portion 62 to receive the legs of a U-shaped clip member 72. The clip member 72 includes opposing legs 74, 76 with the forward ends 78, 80 thereof being tapered. The legs 74, 76 are interconnected by a bight portion 82.

Figure 7:
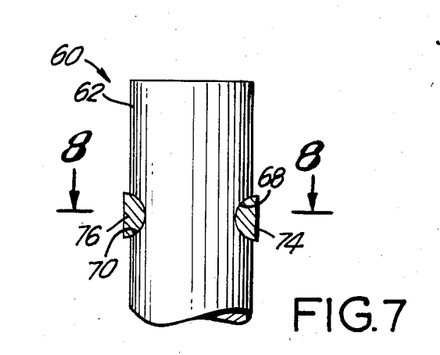
FIG. 7 is an enlarged view of the projecting upper end portion of the dental post shown in FIG. 5, showing a cross section of the clip member straddling the end portion.
Figure 8:
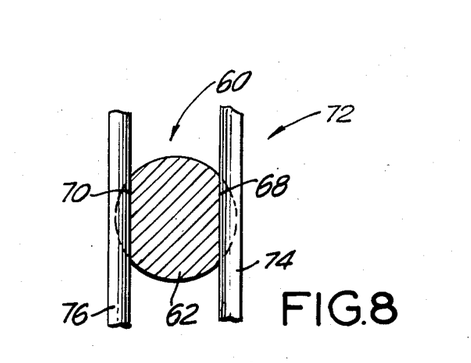
FIG. 8 is a partial sectional view taken along line 8—8 of FIG. 7.

As is best seen in FIGS. 7 and 8, the grooves 68, 70 are less than a semi-circle. In this manner, the semi-circular legs 74, 76 are only partially received within the grooves 68, 70, so that a portion of the legs project from the peripheral surface of the end portion 62 of the dental post 60. These projecting portions of the legs will mate with a groove pattern within a dental core to permit the U-shaped clip to interlock the core to the dental post.

Figure 6:
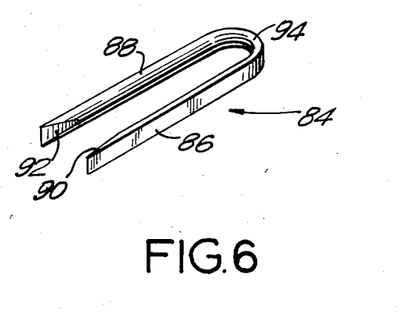
FIG. 6 is a perspective of another embodiment of the clip member shown in FIG. 5.

As shown in FIG. 6, a U-shaped clip member 84 can be formed with legs 86 and 88, with the leg 88 being shorter than the leg 86. Again, the forward ends 90, 92 are tapered. A bight portion 94 interconnects the legs 86, 88. The clip member 84, like the clip member 72, formed of a half-round stock cross section, with the flat surface being on the outer face.

Each of the U-shaped clip members shown in FIGS. 1-4 or FIGS. 5-8 can be utilized in a manner to be hereinafter described as part of an interlock arrangement to connect a metallic dental core to a dental post.

Figure 9:
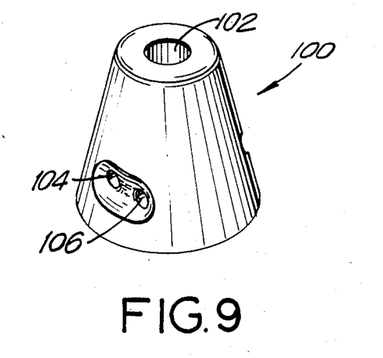
FIG. 9 is a perspective view of a preformed plastic core for use with the dental post and clip member of the present invention.
Figure 10:
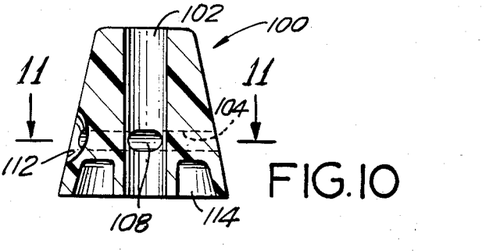
FIG. 10 is a vertical cross sectional view of the preformed plastic core shown in FIG. 9.
Figure 11:
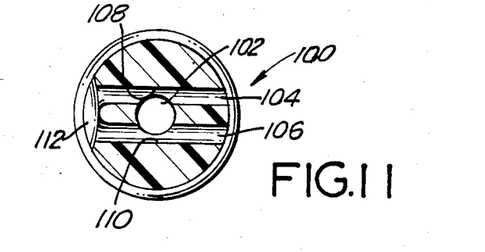
FIG. 11 is a cross sectional view taken along line 11—11 of FIG. 10.

One method of forming the dental core will now be described in connection with FIGS. 9-19. In this method, there is provided a pre-formed, plastic core 100. The plastic core 100 is shown in FIG. 9 to be of substantially frusto-conical configuration including an axial central bore 102 for receiving the upper end portion of the dental post. A pair of spaced apart transverse channels 104, 106 are formed through the plastic core 100 to substantially straddle the central bore 102. As best shown in FIGS. 10 and 11, the transverse channels 104, 106 intersect the central bore 102 to define groove portions 108, 110. These groove portions 108, 110 define the mating portions to the grooves formed in the upper end portion of the dental post for receiving the legs of the U-shaped clip member. In this manner, a portion of each leg of the U-shaped clip member will be received within the dental post, and the remaining part of the portion of each leg of the dental clip member will be received within the groove portions 108, 110, where the rest of the legs are received in the channels 104, 106.

At the mouth of the channels 104, 106, there is provided a recess 112 which can receive the bight portion of the U-shaped clip member. A circular bottom recess 114 is upwardly formed into the bottom surface of the plastic core 100 around the bottom wall portion of the bore 102 for receiving wax and/or cement during the formation of the metal core, as will hereinafter be described.

The particular frustroconical shape shown in FIGS. 9-11 is of particular use in connection with an anterior profile tooth. However, for a posterior profile, other shapes can be used, for example, the embodiment shown in FIG. 12 will find better use. More particularly, in the cross section of FIG. 12, there is shown a pre-formed plastic core 116 having an axial central bore 118 and a pair of transverse channels 120 which intersect to define groove portions 122. A recess 124 is provided at the mouth of the channels. A circular bottom recess 126 upwardly extends from the bottom of the core 116. The core 116 and parts thereof function in the same manner as described above with respect to the core 100.

Figure 13:
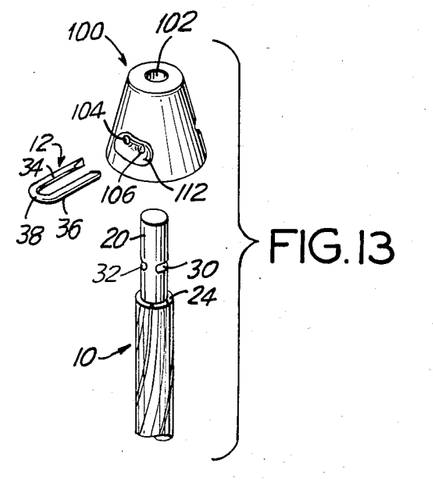
FIG. 13 is an exploded perspective view of the composite dental post system including the dental post, the clip member, and the preformed plastic core for use in the formation of a dental restoration.
Figures 14, 15:
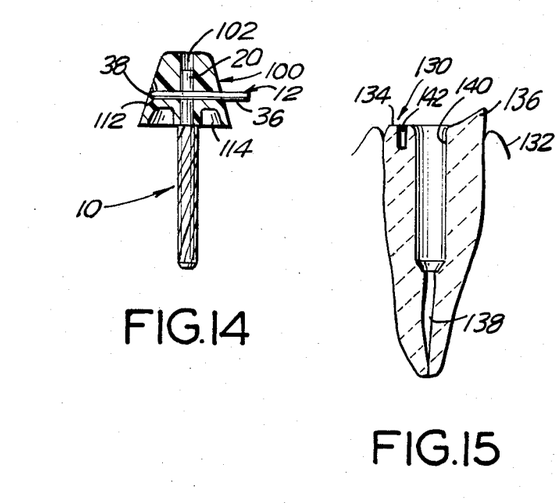
FIG. 14 is a cross sectional view through the assembled dental post system of FIG. 13, showing an initial step in the formation of a metallic core during the dental restoration of devitalized dentition.
FIG. 15 is a cross sectional view taken through a tooth stub showing the preparation of the tooth stub for utilization of the dental post system shown in FIGS. 13 and 14.

The method of utilizing the dental post, the interlock arrangement, and the pre-formed plastic core will now be described. As shown in FIG. 13, the three parts, namely, the dental post 10, the U-shaped clip member 12, and the plastic pre-formed core 100 are assembled as shown in Fig. 14, so that the upper end portion 20 of the dental post 10 is first received within the axial central bore 102 of the pre-formed plastic core 100, and then the U-shaped clip member 12 is inserted into the channels 104, 106. When assembled, the bight portion 38 is received within the recess 112 of the plastic core 100, and the legs 34, 36 extend through the channels 104, 106 so as to project beyond the periphery of the plastic core 100.

Referring now to FIG. 15, a tooth stub 130 is situated within the gum area 132, where upper end of the tooth, not shown, has been broken or decayed. The tooth has been initially cut down and prepared, typically to provide an upper surface 134. The upper surface 134 may not be planar, as is shown by the protrusion 136 left on the upper surface 134 to save as much of the tooth as possible.

After the tooth surface 134 is formed, root canal work is carried out including the cleaning out of the pulp along the apical canal 138 provided in the tooth stub 130. The apical canal 138 is then sealed with gutta percha.

An enlarged bore 140 is drilled into the tooth stub of a size commensurate with the periphery of the dental post to be inserted therein. Generally, a small sized drill is utilized to initiate the drilling of the bore to the desired depth, and then successively larger drills are used to enlarge the bore to the desired diameter and the previously established depth. Typically, the depth of the bore should be ½ to ⅔ the length of the root canal, which can be determined by measurement or by X-ray verification.

At least one auxiliary channel 142 is drilled into the tooth stub 130 by using paralleling jigs well known in the art, so that the channel 142 is parallel to the bore 140. The channel 142 is narrower and shorter than the bore 140, where the function of the channel 142 will be set forth below.

Figure 16:
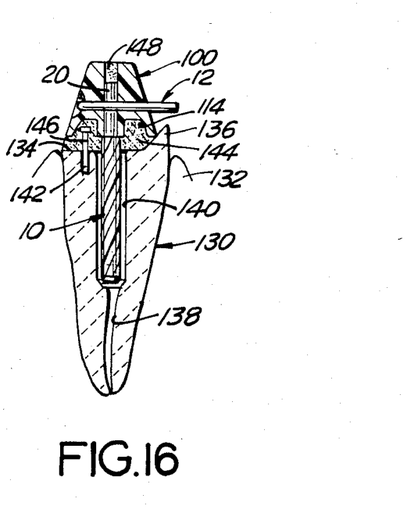
FIG. 16 shows a subsequent step in the formation of a core pattern for the dental restoration, wherein the dental post system of FIG. 14 is inserted into the prepared tooth stub of FIG. 15 with a wax interface therebetween.

As shown in FIG. 16, the dental post, interlock arrangement and pre-formed plastic core assembly of FIG. 14 is inserted into the bore in the tooth stub 162, where preferably the tooth surface, bore and channel have previously been lightly lubricated, and a layer of wax 144 has been placed at the interface between the plastic core 100 and the upper surface 134 of the tooth stub 130. Additionally, a retention pin 146 has been inserted in the channel 142. The wax 144 will enter the bottom recess 114 and surround the upper head portion of the retention pin 146. It should be appreciated that the shoulder 24 of the dental post serves as a stop for entry of the dental post 10 into the bore 102 of the plastic core 100, so that only the upper end portion 20 is received in the core 100, where the core 100 rests on the shoulder 24. Preferably, additional wax 148 is inserted into the bore 102 above the upper end portion 20 to fill the bore 102.

Figure 12:
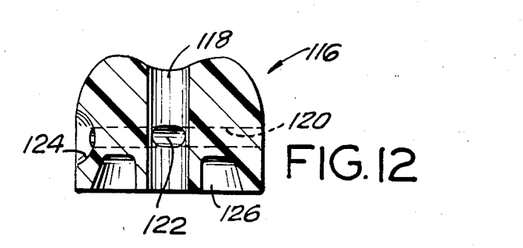
FIG. 12 is a vertical sectional view through another embodiment of a preformed plastic core, for use with a posterior profile tooth.

The pre-formed plastic core can now be appropriately cut and shaped to have its periphery contoured into a desired configuration to which the final metallic core should be cast. The frustro-conical shape is one that is uniquely suited for the anterior teeth and often no further contouring of the periphery is needed. Similarly, the configuration shown in FIG. 12 is uniquely suited for posterior teeth and, again, often no further peripheral contouring would be needed.

After the wax has been hardened, the assembly including the wax and the retention pin is removed from the tooth stub. The clip member 12 is then removed so as to separate the pre-formed plastic core 100, including the wax interface, from the dental post 10. Defined within the plastic core 100 will be the axial central bore 102, closed at the top by the wax 148, to accommodate the upper end portion of the dental post, as well as the transverse channels straddling the central bore 102 to accommodate the legs of the U-shaped clip member, as well as the recess 112 to accommodate the bight portion of the U-shaped clip member. Also, the upper surface configuration of the tooth stub will now be formed into the wax to define a particular pattern required for a metallic core, where the wax will hold the retention pin 146 in a secured position.

The plastic core 100 and the wax including the retention pin 146 are now used as a pattern for the casting of a permanent metallic core. Such casting methods are well known in the dental art, wherein the metallic core is investment cast from the core pattern just formed. In such procedures, the core pattern is invested in a plaster material, or the like. The core pattern is then melted out to leave a plaster mold. A suitably precious or non-precious material, typically used in a dental cast, is then poured into the mold. After setting, the mold is broken away, leaving the cast metallic core. Typically, gold, or the like, could be utilized for such metallic casting of the core. It is understood that the casting procedure is complicated and does not form a part of the present invention, where the above is just a brief description thereof.

Figure 17:
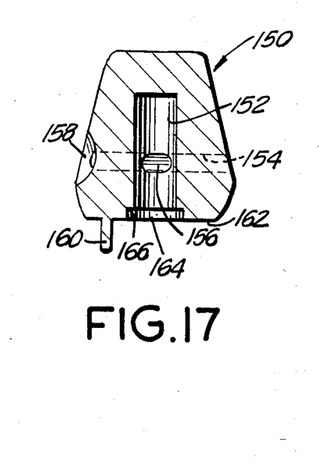
FIG. 17 is an enlarged elevational sectional view taken through a cast metallic core formed from the core pattern of FIG. 16.

As shown in FIG. 17, the metallic cast core 150 has been formed including a central bore 152 closed at the top thereof, a pair of transverse channels 154 which intersect the bore 152 to define groove portions 156, a recess 158 at the mouth of the channels 154, a retention pin portion 160, and the contouring along the lower surface 162 conforming to the upper surface 134 of the tooth stub 130. At the same time, a recess 164 is now formed to provide a shoulder stop 166, as will be described below. The recess 164 results from the fact that the shoulder portion 24 of the dental post 10 abutted the lower surface of the preformed plastic core 100. However, because of the presence of the wax 144, the shoulder portion 24 was upwardly spaced from the surface 134 of the tooth stub 130. Since the fluted portion of the dental post 10 is slightly of greater diameter than the upper end portion 20, this wider fluted portion was formed within the wax 144, as shown in FIG. 16. As a result, the cast metallic core 150 now includes this wider section, formed by the fluted portion, as the recess 164 in the lower surface of the metallic core 150.

Figure 18:
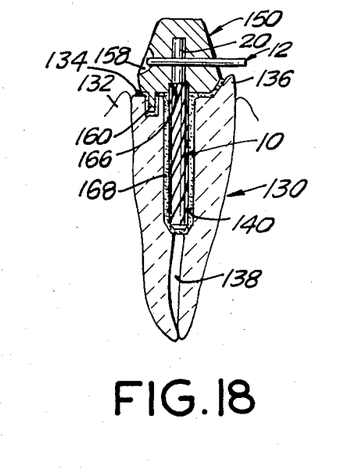
FIG. 18 is a cross sectional view similar to that shown in FIG. 16 with the cast metallic core positioned on the tooth stub over the projecting upper end of the dental post, with the clip member reinserted to lock the cast metallic core in place.

The cast metallic core 150 is ready to be positioned on top of the tooth stub 130, as shown in FIG. 18. Either before or after the dental post 10 is inserted into the bore 140 in the tooth stub 130, the U-shaped clip member 12 is inserted into the channels 154 when the core 150 is mounted on the dental post 10, so as to lock the cast metallic core 150 to the upper end portion 20 of the dental post, where the shoulder stop 166 limits the insertion of the dental post 10 into the core 150. The legs of the clip member 12 straddle the end portion 20 of the dental post, with the thickness of the legs 34, 36 being partially received within the grooves 30, 32 in the end portion 20 and being partially received within the corresponding mating groove portions 156 now cast in the metallic core 150. In this manner, the metallic core 150 is locked in place onto the upper end portion 20 of the dental post 10, where if desired, cement can additionally be applied between the end portion 20 and the metallic core 150.

Cement 168 is used to permanently secure the cast metallic core 150 onto the upper surface 134 of the tooth stub 130, and similarly, the cement 168 fills the bore 140 to securely retain the dental post 10 in the bore 140, and also fills the channel 142 to securely retain the retention pin portion 160 in the channel 142. It is noted, that the retention pin portion 160 is used for additional retention of the core 150, and to prevent rotational movement of the core 150 relative to the tooth stub 130.

The ends of the dental clip member, specifically the end portions of the legs extending beyond the periphery of the metal cast core 150, are now cut off to make the clip member flush with the peripheral surface of the cast metallic core 150.

Figure 19:
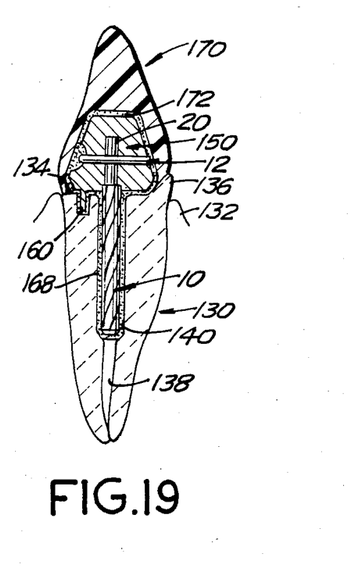
FIG. 19 is a cross sectional view similar to that shown in FIG. 18, showing the end of the clip cut flush with the edge of the cast metallic core, and with a dental restoration fabricated on the metallic core.

As shown in FIG. 19, a dental restorative member 170 is built up or mounted onto the core 150 and secured in place by means of appropriate cement 172, as is well known in the art. It is noted, that the cement 172 fills in the recess 158 of the core 150.

It should be appreciated, that the dental post 10 could be cemented in place initially as soon as it is first inserted into the bore 140, as for example as shown in FIG. 16, when the pre-formed plastic core 100 is mounted thereon. Alternately, the dental post 10 can be cemented in place, as shown in FIG. 18, after the metallic cast core 150 has been formed, either before or after the core 150 is interlocked to the dental post 10.

With the above method described, benefits over all prior known techniques are achieved. Specifically, the initial dental post that is originally inserted in the tooth bore can be retained for actual subsequent use in the patient's tooth. There is no need to continuously reinsert various dental posts, some of which are temporary, others of which are permanent.

Furthermore, and most important, there is provided the ability for the casting of a metallic core without the need of casting that core in a unitary one piece fashion together with the dental post. The dental post is maintained separate from the core and can be fabricated from a different type of metal, where only subsequently are they interlocked together, which is after the metallic core has been appropriately cast in accordance with a desired shape.

In the embodiment described above, the formation of the metallic core 150 was facilitated through the use of a pre-formed plastic core 100 forming the basic structure from which the metallic core was obtained. However, in a second embodiment, such a plastic core need not be utilized, where the metallic core could be obtained from a core pattern built up directly onto the dental post in the patient's mouth.

Figure 20:
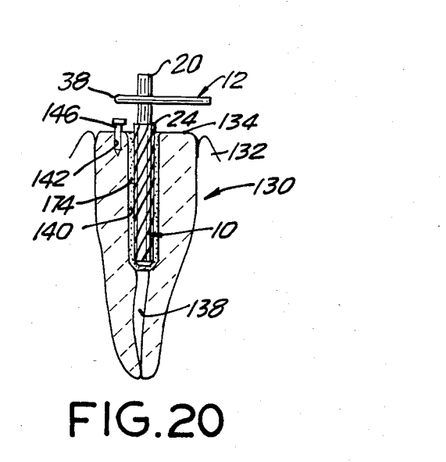
FIG. 20 is a cross sectional view through a prepared tooth stub showing another embodiment in the preparation of the metallic core without the use of a preformed plastic core.

More particularly, referring now to FIGS. 20-25, there is described such a second embodiment. The initial preparation of the tooth stub 130 would be as heretofore described in connection with FIG. 15. More particularly, root canal work would be carried out, the apical canal 138 would be sealed, the bore 140 would be suitably formed of an appropriate size commensurate with the dental post to be inserted, and the auxiliary channel 142 would be drilled into the tooth stub 130 parallel to the bore 140. The upper surface 134 of the tooth stub 130 would be appropriately prepared where the upper surface 134 can be planar as shown in FIG. 20, without the protrusion 135 shown in FIG. 15.

The dental post 10 is then inserted into the bore 140 with the U-shaped clip member 12 straddling the upper end portion 20 on the dental post 10. In the embodiment shown, the dental post 10 is cemented into the bore 140 through the use of standard cement 174. However, as heretofore explained, the cementing of the post 10 could be achieved subsequently after the metallic core has been cast, either before or after the metallic core is interlocked to the dental post 10.

The dental post 10 is inserted so that its upper end portion 20 and shoulder 24 extend above the surface 134 of the tooth stub 130. A portion of the fluted portion, slightly below the shoulder 24, also extends above the surface 134. The retention pin 146 is inserted in the channel 142 so that the upper head portion of the retention pin 146 extends above the surface 134.

Figure 21:
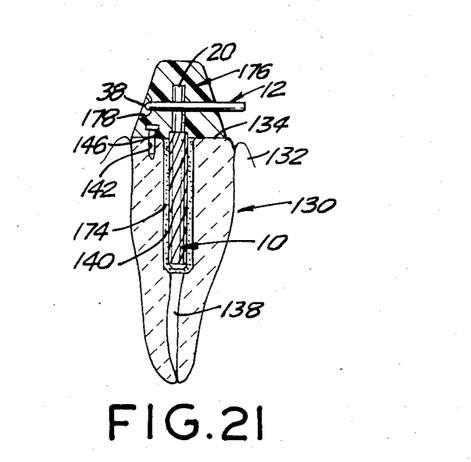
FIG. 21 is a cross sectional view similar to that shown in FIG. 20, showing the formation of a core pattern of impression material on the tooth stub.

As shown in FIG. 21, a core 176 is now built up with impression material onto the upper surface 134 of the tooth stub 130, the core 176 encompassing the upper end portion 20 of the dental post 10 and the upper head portion of the retention pin 146. The clip member 12 remains in place and is enclosed by the impression material. However, the length of the clip member 12 is such as to extend beyond the periphery of the core 176. The legs of the U-shaped clip 12 are therefore projecting from the surface of the core 176. A recess 178 is formed to accommodate the bight portion 38 of the U-shaped clip member 12. The core 176 is formed of amalgam, composite material, resin, or the like impression material, as is well known in the art.

Figure 22:
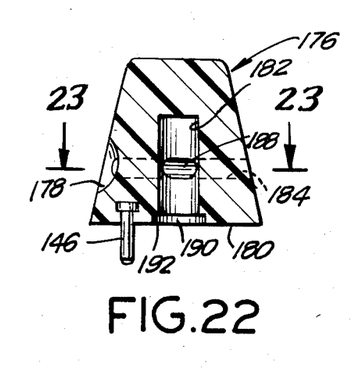
FIG. 22 is an enlarged elevational view taken through the core pattern formed in FIG. 21 with the clip and dental post removed.
Figure 23:
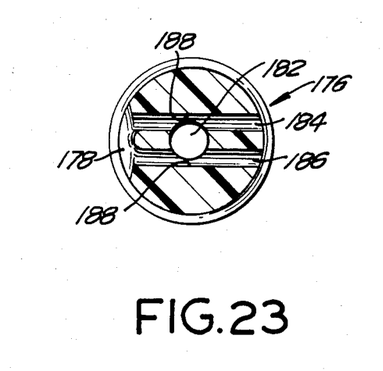
FIG. 23 is a cross sectional view taken along line 23—23 of FIG. 22.

After the impression material of the core 176 has been properly shaped, as desired, the clip member 12 is extracted from the core 176 and the upper end portion 20. The core 176, including the retention pin 146, can then be removed and will form the configuration as shown in FIGS. 22 and 23.

Specifically, the core 176 will have its lower surface 180 conform to the upper surface 134 of the tooth stub 130, with the retention pin 146 extending outwardly therefrom. It will include a central bore 182 for accommodating the upper end portion 20 of the dental post 10. It will also include the recess 178 to accommodate the bight portion 38 of the clip member 12, and a pair of laterally spaced transverse channels 184, 186 to accommodate the legs of the U-shaped clip member 12, where the channels 184, 186 intersect the bore 182 to define groove portions 188. A recess 190 will also be formed in the lower surface 180 to accommodate the wider anchor portion of the dental post 10, which is slightly extending above the tooth surface 134. The recess 190 provides a shoulder stop 192, similar to the shoulder stop 166 described above.

The core 176 is then used as the pattern for the casting of a permanent metallic core 194. Such casting can again use the casting method heretofore described. Appropriate precious or non-precious material will be used to form the final cast metallic core 194. The metallic core 194 is structurally similar to the above metallic core 150 shown in FIG. 17, so that a detailed description of the metallic core 194 is not necessary.

Figure 24:
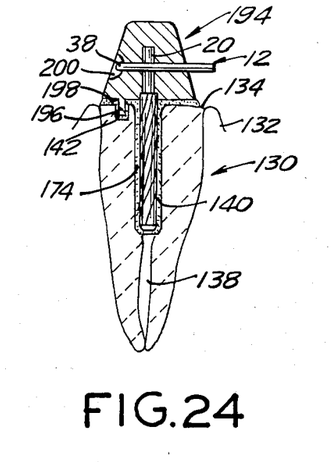
FIG. 24 is a cross sectional view similar to that shown in FIG. 21 with the cast metallic core positioned on the tooth stub over the projecting upper end of the dental post, with the clip reinserted to lock the cast metallic core in place.

Referring now to FIG. 24, which is similar to FIG. 18, the metallic cast core 194 is mounted onto the top surface 134 of the tooth stub 130 so as to sit onto the upper end portion 20 of the dental post 10, with the retention pin portion 196 of the core 194 extending into the channel 142 in the tooth stub 130. Suitable cement 198 is utilized to securely retain the metallic core 194 onto the upper surface 134 of the tooth stub, and also to retain the retention pin portion 196. The clip member 12 is inserted through the appropriately cast channels in the metallic core 194 to again straddle the upper end portion 20 of the dental post 10, with bight portion 38 being received in the core recess 200. In the vicinity of the dental post, a portion of each of the legs of the clip member 12 is retained in place by the grooves in the upper end portion 20 of the dental post and the corresponding mating grooves now cast into the metallic core 194. In this manner, the metallic core 194 is secured in place onto the upper surface 134 of the tooth stub 130, being locked onto the upper end portion 20 of the dental post 10.

The clip member 12 again extends beyond the surface of the metallic core 194. The legs 34, 36 of the clip member can then be cut off so as to conform to the peripheral surface of the cast metallic core 194.

Figure 25:
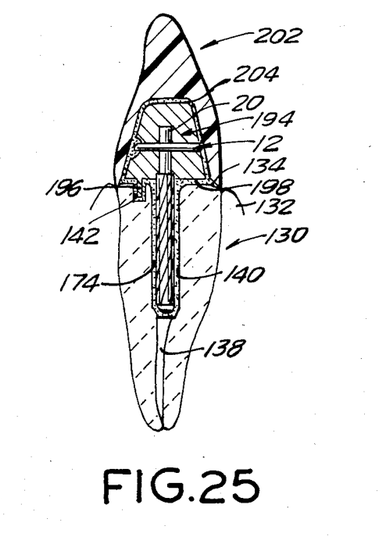
FIG. 25 is a cross sectional view similar to that shown in FIG. 24 showing the end of the clip cut flush with the edge of the cast metallic core, and with a dental restoration fabricated on the metallic core.

As shown in FIG. 25, which is similar to FIG. 19, a suitable dental superstructure 202 can then be formed or mounted onto the core 194 and appropriately shaped to provide the restorative dentistry needed. Cement 204 can be utilized to secure the superstructure 202 onto the core 194, where the cement 204 fills the core recess 200.

With the method shown in FIGS. 20-25, the benefits of both the use of a dental post which is secured into the tooth, as well as the use of the casting of the metal core can be achieved. The benefits result from the interlock arrangement, where the metallic cast core of one type of metal can be secured onto the dental post of a different type of metal. The metallic core can be cast without the need of simultaneously casting the dental post directly therewith as a one piece unit, such one piece unit being required in the prior dental art.

The particular interlock arrangement, heretofore described, utilized a U-shaped clip member in conjunction with a pair of grooves straddling the upper end portion of the dental post. However, other types of interlock arrangements can be utilized in order to secure the cast metallic core onto the dental post. These interlock arrangements can be used either in conjunction with a pre-formed plastic core or can be used where the initial core pattern is formed from dental impression material such as amalgum, composite, and the like. For ease of explanation, however, the various alternate embodiments of the interlock arrangement will hereinafter be described in conjunction with a pre-formed plastic core, where it is understood that the core pattern could also be formed in the manner described above and shown in FIGS. 20-23.

Figure 26:
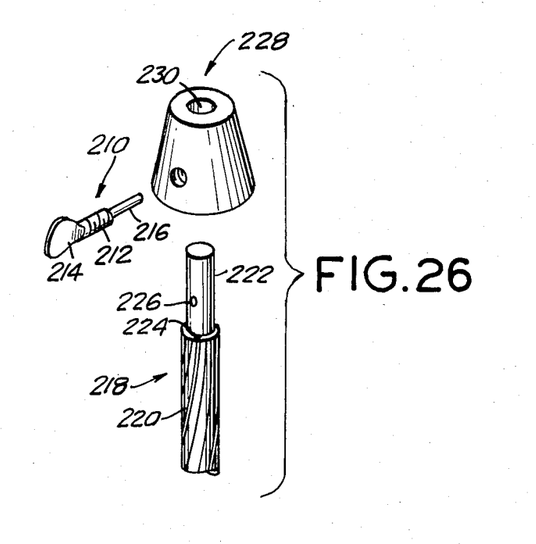
FIG. 26 is an exploded perspective view of yet another dental post system showing the use of a partially threaded cross pin in conjunction with a preformed plastic core to provide the interlock arrangement between the core and the dental post.
Figure 27:
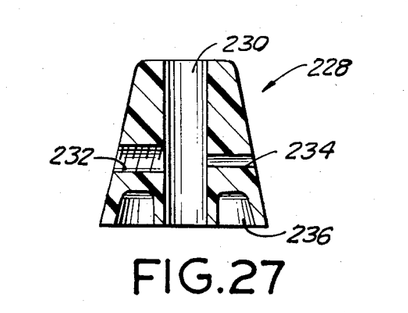
FIG. 27 is an elevational cross sectional view through the preformed plastic core of FIG. 26 for use in restoring an anterior profile tooth.

As shown in FIGS. 26 and 27, the interlock arrangement uses a cross pin, shown generally at 210. The cross pin 210 includes a substantially cylindrical body portion 212 externally threaded and having a flattened tang 214 at one end thereof. A reduced elongated cylindrical rod 216 projects from the opposite end of the body portion 212. The dental post 218 includes a fluted lower anchor portion 220 and an upper end portion 222 separated by a radially projecting shoulder 224, which at this point is similar to the above mentioned dental post 10. A bore 226 transversely extends entirely through the upper end portion 222, which replaces the above mentioned channels or grooves 30, 32.

The pre-formed plastic core 228 is shown of substantially frustoconical configuration and includes an axially extending central bore 230 to receive the upper end portion 222 of the dental post 218. Preferably, but not necessarily, the upper end portion 222 of the post is the same length as the bore 230 of the core. A laterally extending aperture is formed through the plastic core 228 which intersects the central bore 230. On one side of the central bore 230, the aperture is threaded at 232 and is substantially of greater diameter than the smooth portion 234 of the aperture on the other side of the central bore 304. A circular recess 236 is formed into the bottom of the plastic core 228 to accommodate the receipt of wax and cement material, as mentioned above.

The interlock is arranged so that the plastic core 228 fits onto the dental post 218, and the cross pin 210 is threaded into the threaded aperture portion 232 of the core 228 and passes through the bore 226 of the post into the smooth aperture portion 234 to interlock the core to the post. The particular core pattern will be formed and cast into the metallic core in the manner described above, so that the same type of cross pin will be used to lock the metallic core onto the dental post.

Figure 28:
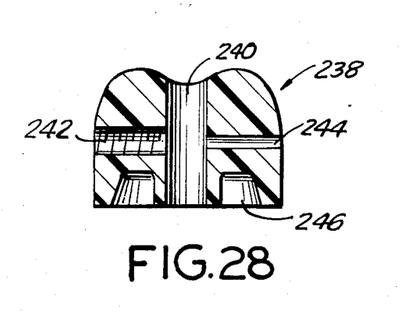
FIG. 28 is an elevational cross sectional view through a preformed plastic core, similar to that shown in FIG. 27, for use with the interlock arrangement shown in FIG. 26, when a posterior profile tooth is being restored.

As shown in FIG. 28, a similar type of interlock arrangement can also be used with a posterior profile. In this latter case, the plastic core 238 is shown to include a central bore 240, a threaded aperture portion 242 on one side thereof, and a smooth, smaller diameter, aperture portion 244 on the other side of the central bore 240. An appropriate circular recess 246 is provided into the bottom of the core 238.

It would be appreciated, that all of the interlocking arrangements can be used in connection with the frustoconical shaped core, the posterior profile shaped core or, as heretofore mentioned, can be used with the impression material core formed out of composite material, amalgum, etc.

Figure 29:
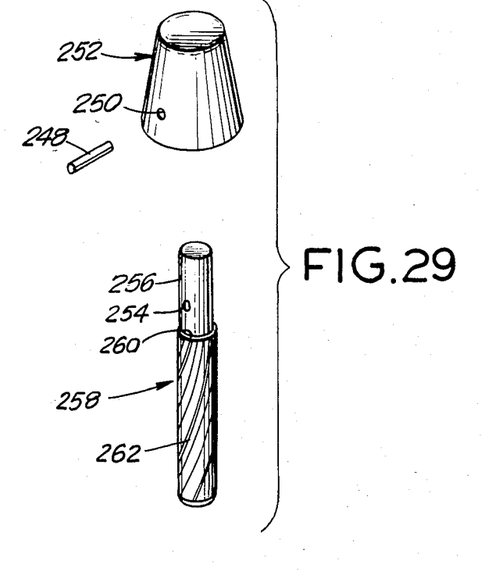
FIG. 29 is an exploded perspective view of another dental post system using an anti-rotational pin for the interlock between the dental post and core, showing the use of a preformed plastic core for use with such interlock arrangement.
Figure 30:
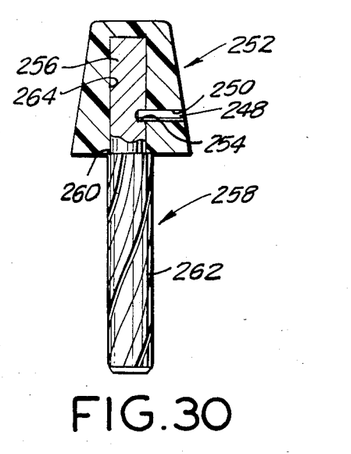
FIG. 30 is an elevational cross sectional view through the assembled parts of FIG. 29.

The interlock arrangement shown in FIGS. 29 and 30 makes use of an anti-rotational pin 248 which can be inserted into the aperture 250 formed into the plastic core 252. A detent 254 is formed in the upper end portion 256 of the dental post 258 to receive the end of the pin 248. The shoulder 260 separates the upper end portion 256 from the fluted bottom portion 262.

It will be noted, that the upper end portion 256 is preferably slightly shorter than heretofore described embodiment of FIG. 26. As best seen in FIG. 30, the bore 264 formed in the central portion of the plastic core 252 does not extend entirely therethrough, but only extends upwardly from the bottom portion thereof. The bore 264 forms a seat for receiving the upper end portion 256 of the post. However, it is understood that even though the upper end portion 256 is shorter, the bore 264 can extend through the core 252 to function as shown in FIGS. 13, 14 and 16.

When the actual metallic core will be cast, the upper end portion 256 will be cemented into the correspondingly formed bore of the metallic core. The pin 248 will then serve as an anti-rotational pin for locking the metallic core to the upper end portion 256 of the dental post when the pin 248 is received in the post detent 254.

Figure 31:
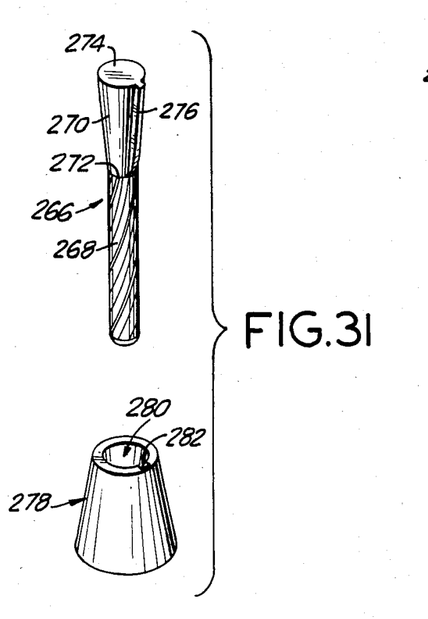
FIG. 31 is an exploded perspective view of yet another dental post system, showing the use of a tapered lock with an anti-rotational key in combination with a preformed plastic core.
Figure 32:
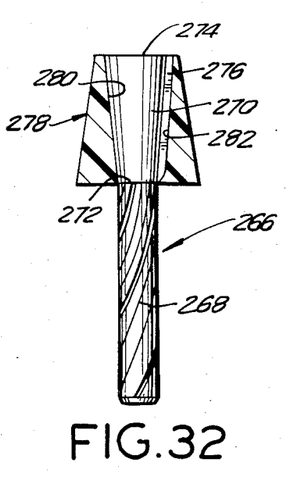
FIG. 32 is an elevational cross sectional view through the assembled parts of FIG. 31.
Figure 33:
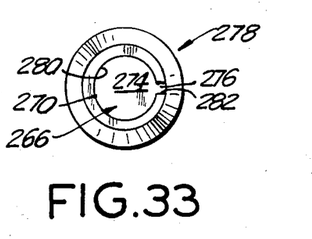
FIG. 33 is a top view of the assembled parts of FIG. 32.

As shown in FIGS. 31–33, the interlock arrangement includes a taper-holding lock with an anti-rotational key. More specifically, the dental post 266 includes a lower fluted portion 268. The upper end or head portion 270 is outwardly tapered from the neck 272 to the top 274 thereof, so that the top 274 is greater than the neck 272. At the same time, a longitudinally extending radially directed key 276 projects from the periphery of the tapered head portion 270.

The pre-formed plastic core 278 includes a tapered central bore 280 to accommodate the shape of the tapered head portion 270 of the dental post. An elongated radially extending keyway 282 is provided into the plastic core 278 to accommodate the projecting key 276 on the head portion 270.

With the arrangement shown, the plastic core 278 would be placed on the tooth surface either before or after the dental post 266 is inserted through the core 278. The plastic core 278 would be configured and shaped as desired to form a core pattern, and then the metallic core would be cast therefrom. In assembling the metallic core to the dental post, again the metallic cast core would be placed on the tooth stub surface either before or after the dental post 266 is inserted through the metallic core.

By means of the tapered arrangement, the metallic core cannot be moved upwardly once the post is secured in the tooth stub. Furthermore, the key arrangement prevents any rotation between the metallic core and the dental post, therefore there is no rotation between the metallic core and the tooth stub once the post is secured in the tooth stub.

Figure 34:
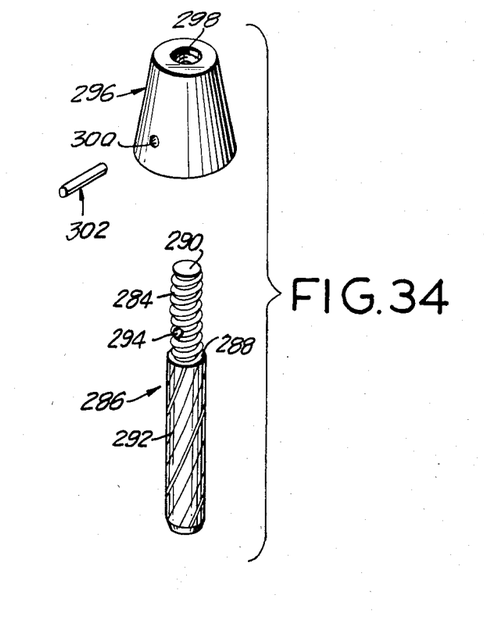
FIG. 34 is an exploded perspective view of yet another dental post assembly showing the use of a thread lock and an anti-rotational pin in combination with a preformed plastic core.
Figure 35:
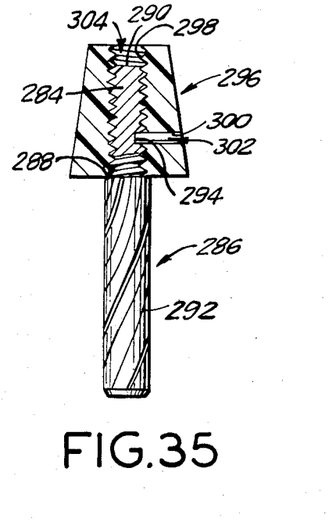
FIG. 35 is an elevational cross sectional view through the assembled parts of FIG. 34.

FIGS. 34 and 35 show yet another form of the interlock arrangement. In this case, the upper end portion 284 of the dental post 286 is threaded from the shoulder 288 to the top 290. The fluted portion 292 is provided below the shoulder 288. A detent 294 is also provided into the upper end portion 284.

The pre-formed plastic core 296 is formed with a threaded axially extending central bore 298 passing entirely therethrough to receive the threaded upper end portion 284 of the dental post 286. A radially extending aperture 300 is provided, extending partially therethrough for communication with the central bore 298. An anti-rotational pin 302 is also provided.

The locking arrangement is such that the upper end portion 284 of the dental post 286 is threaded into the threaded bore 298 of the core 296, and the anti-rotational pin 302 is inserted through the aperture 300 into the detent 294 to prevent rotation of the core 296 with respect to the post 286, so that the core 296 cannot be removed from the dental post 286.

As shown in FIG. 35, the length of the upper end portion 284 is less than the length of the central bore 298, to provide a space 304 at the top thereof, similar to that shown in some of the previous embodiments. However, it is understood, that if desired, the upper end portion 284 could be made the same length as the central bore 298, as also shown above in some of the embodiments.

Figure 36:
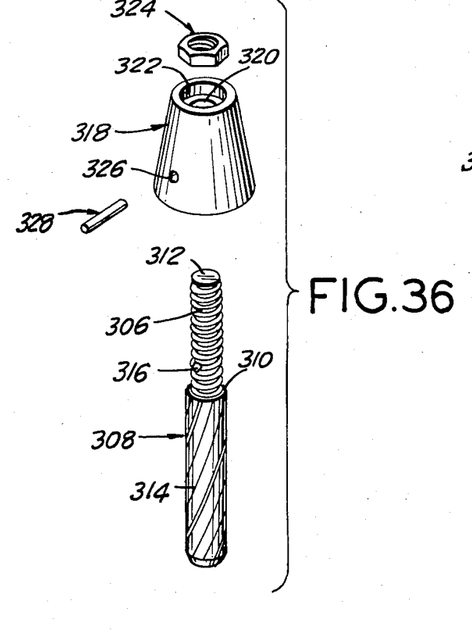
FIG. 36 is an exploded perspective view of a modified form of the dental post assembly of FIG. 34, where a lock nut is used instead of internally threading the preformed plastic core.

FIG. 36 shows a further modification of the interlock arrangement shown in FIGS. 34, 35. In this modification, the upper end portion 306 of the dental post 308 is again threaded from the shoulder 310 to the top 312. However, as will be explained below, the upper end portion 306 is made longer. Again, a fluted portion 314 is provided below the shoulder 310, and a detent 316 is provided into the upper end portion 306.

The pre-formed plastic core 318 is again provided with an axially extending central bore 320 passing entirely therethrough to receive the threaded upper end portion 306 of the dental post 208. The central bore 320 is the same length as the upper end portion 306. However, the central bore 320 is not threaded. In place of the threading, the central bore 320 is provided with an enlarged recess 322 to received a threaded nut 324 therein. A radially extending aperture 326 is again provided, extending partially therethrough for communication with the central bore 320. An anti-rotational pin 328 is again also provided.

The locking arrangement is such that the upper end portion 306 of the dental post 308 is inserted through the central bore 320 of the core 318 so that the nut 324 can be threaded onto the top of the upper end portion 306 when the nut 324 is received in the recess 322. The anti-rotational pin 328 is then inserted through the aperture 326 into the detent 316 to prevent rotation of the core 318 with respect to the post 308, so that the core 318 cannot be removed from the dental post 308.

Figure 37:
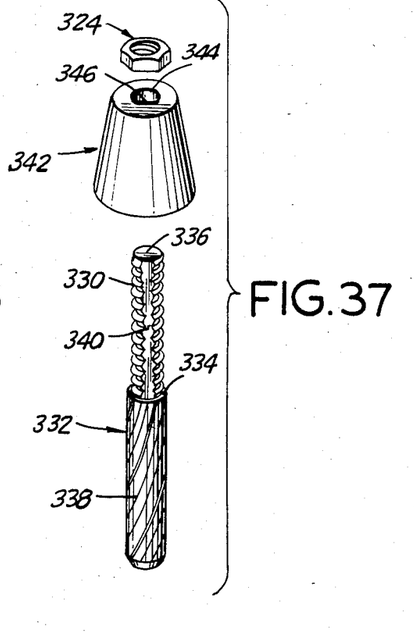
FIG. 37 is an exploded perspective view of a modified form of the dental post assembly of FIG. 36, where a flat is provided between the dental post and the preformed plastic core instead of the anti-rotational pin.

FIG. 27 shows yet another modified form of the interlock arrangement shown in FIG. 36. In this case, the upper end portion 330 of the dental post 332 is again threaded from the shoulder 334 to the top 336. The fluted portion 338 is again provided below the shoulder 334. However, no detent is provided in this modification, where in place of such detent, the upper end portion 330 is provided with an axially extending flat portion 340, the function of which will be explained below.

The pre-formed plastic core 342 is again formed with an axially extending central bore 344 passing entirely therethrough to receive the threaded upper end portion 330 of the dental post 332. However, no radially extending aperture is provided, where in place of such anti-rotational arrangement, an axially extending flat wall portion 346 is provided in the central bore 344. Again, the nut 324 is provided.

The locking arrangement is such that the upper end portion 330 of the dental post 332 is inserted into the central bore 344 with the flat portion 340 of the post 332 and the flat wall portion 346 of the core 342 being in mating engagement with each other so that the core 342 cannot rotate relative to the dental post 332. Preferably, to avoid the necessity of the recess 322 of FIG. 36, the upper end portion 330 of the dental post 332 is made longer to extend outwardly from the central bore 344 of the core 342. Accordingly, the nut 324 is secured onto this extending portion of the upper end portion 330 to secure the core 342 to the dental post 332. Obviously, if desired, the above mentioned recess can be provided in the core 342.

It is noted, that the anti-rotational pins shown in FIGS. 30 and 35 are flush with the outer surface of the core. However, these anti-rotational pins are preferably made longer to extend beyond the outer surface of the core so that they can be easily removed. Accordingly, once these anti-rotational pins are inserted into the metal core, then the extending portions thereof are cut off so that these anti-rotational pins in their final state would be flush with the outer surface of the metal core as shown in FIGS. 30, 35.

It should be appreciated that all of the interlock arrangements that have been described above will prevent axial lift-off of the metallic core with respect to the dental post, as well as preventing rotation between the metallic core and the dental post, so that when the dental post is secured in the tooth stub, the metallic core will also be secured relative to the tooth stub.

Any of the various interlocking arrangements could be used in conjunction with any of the previously described methods for forming the metallic cast core, either through the use of a pre-formed plastic core or by using an impression material in the building up of a core pattern. Also, it should be appreciated that the dental post can either be initially cemented in place in the tooth stub or cemented subsequently in place in the tooth stub either before or after its interlock with the metallic core.

Numerous alternatives of the structures herein disclosed will suggest themselves to those skilled in the art. However, it is to be understood that the present disclosure relates to preferred embodiments of the present invention which are for the purpose of illustration only and are not to be construed as a limitation of the present invention.

What is claimed is:

1. A dental post system for use in preparing a dental restoration, comprising:
    a dental core;
    an elongated cylindrical post having a lower anchoring portion for secured retention within a cement prepared bore in a tooth stub, and an upper end portion for projecting from the tooth stub to be received within an aperture in said dental core, the restoration being disposed on said dental core;
    interlock means for securing said dental core onto said upper end portion of said cylindrical post to prevent both axial lift-off as well as rotational displacement between said dental core and said cylindrical post; and
    a laterally extending shoulder portion being provided on said cylindrical post between said lower anchoring portion and said upper end portion to define stop means for engaging said dental core to prevent insertion of said lower anchoring portion into said aperture of said dental core so that said dentral core is positioned on said upper end portion at a predetermined location to permit coaction between said interlock means and said upper end portion.

2. A dental post system as in claim 1, wherein said interlock means includes a substantially U-shaped clip member having a pair of opposing legs and a bight portion; and
    a pair of grooves provided in opposing sides of said upper end portion of said post for receiving said legs of said clip member therein as said clip member transversely straddles said upper end portion, thereby locking said dental core onto said upper end portion, whereby a portion of said clip member is disposed in said dental core.

3. A dental post system as in claim 2, wherein said clip member is a continuous wire bent into a U-shape.

4. A dental post as in claim 3, wherein said wire has a circular cross section.

5. A dental post as in claim 3, wherein said wire has a semi-circular cross section.

6. A dental post as in claim 5, wherein outer surfaces of said wire are substantially flat.

7. A dental post system as in claim 2, wherein one leg of said clip member is shorter than the other leg to facilitate insertion into said grooves.

8. A dental post system as in claim 2, wherein distal ends of said legs are tapered.

9. A dental post system as in claim 2, wherein each of said legs of said clip member has a transverse cross section larger than transverse depth of each associated one of said grooves of said post so that said legs transversely project outwardly from said grooves, respectively.

10. A dental post system as in claim 2, wherein each of said legs of said clip member has a length greater than the diameter of said post so as to transversely extend beyond said upper end portion of said post.

11. A dental post system as in claim 1, wherein said lower anchoring portion includes a plurality of externally spaced apart helical flutes longitudinally disposed about the longitudinal axis of said post for retaining said lower anchoring portion within the cement prepared bore and also for providing a vent for said post when being inserted into the cement prepared bore.

12. A dental post system as in claim 1, wherein at least a major portion of said upper end portion of said post has a smooth cylindrical periphery.

13. A dental post system as in claim 1, wherein said interlock means includes an elongated cross pin, and an aperture transversely extending into said upper end portion of said post for receiving a portion of said cross pin therein, thereby locking said dental core onto said upper end portion, whereby another portion of said cross pin is disposed in said dental core.

14. A dental post system as in claim 13, wherein said cross pin includes an elongated threaded body portion, a removable flattened tang on one end of said threaded body portion, and a rod on an opposite end of said threaded body portion, said aperture extending entirely through said upper end portion and receiving at least a part of said rod, said threaded body portion being disposed in a mating internally threaded bore provided in said dental core.

15. A dental post system as in claim 13, wherein said cross pin includes a smooth cylindrical rod, and said aperture in said upper end portion includes a detent for receiving a forward end of said rod.

16. A dental post system as in claim 15, wherein said upper end portion is externally threaded for engaging a mating internally threaded bore defining said aperture provided in said dental core.

17. A dental post system as in claim 15, wherein said upper end portion has a smooth cylindrical periphery for being received within a blind bore defining said aperture provided in said dental core.

18. A dental post system as in claim 15, wherein said upper end portion is externally threaded for engaging in an internally threaded nut to secured said upper end portion in said aperture provided in said dental core.

19. A dental post system as in claim 1, wherein said interlock means includes said upper end portion being externally threaded with a flat surface across a portion of said threaded upper end portion, and said aperture provided in said dental core having a flat wall matingly engaging said flat surface, and an internally threaded nut threaded onto said threaded upper end portion to secure said upper end portion in said aperture.

20. A dental post system as in claim 1, and further comprising a pre-formed plastic core including an embedded mating pattern for engaging with said interlock means, said plastic core being mounted onto the tooth stub to obtain a core pattern for casting said dental core.

21. A dental post system as in claim 20, wherein a central bore is provided in said pre-formed plastic core for receiving therein said upper end portion of said post.

22. A dental post system as in claim 20, wherein said pre-formed plastic core is of frustoconical shape.

23. A dental post system as in claim 20, and including recess means provided in a bottom surface of said pre-formed plastic core to receive wax therein to improve the contour shape of said plastic core.

24. A dental post system as in claim 21, wherein a pair of transverse channels are provided through said pre-formed plastic core, said channels straddling and partially intersecting said control bore for receiving opposing legs of a substantially U-shaped clip member inserted therein for locking said plastic core to said cylindrical post, and a recess provided in one wall of said pre-formed plastic core at the mouths of said channels for receiving a bight portion of said clip member.

25. A dental post system as in claim 21, wherein a transverse channel is provided in said pre-formed plastic core, said channel intersecting said central bore for receiving a cross pin inserted therethrough for locking said plastic core to said cylindrical post.

26. A dental post system as in claim 25, wherein said transverse channel extends entirely through said plastic core, a channel portion on one side of said central bore being internally threaded and larger than a channel portion on the other side of said central bore.

27. A dental post system as in claim 21, wherein said central bore extends entirely through said preformed plastic core and is internally threaded.

28. A dental post system as in claim 21, wherein said central bore in smooth and extends only partially upward from a bottom portion of said pre-formed plastic core.

29. A dental post system for use in preparing a dental restoration, comprising:
a dental core;
an elongated cylindrical post having a lower anchoring portion for secured retention within a cement prepared bore in a tooth stub, and an upper end portion for projecting from the tooth stub to be received within an aoerture in said dental core, the restoration being disposed on said dental core;
interlock means for securing said dental core onto said upper end portion of said cylindrical post to prevent both axial lift-off as well as rotational displacement between said dental core and said cylindrical post;
a neck portion being provided around said cylindrical post between said lower anchoring portion and said upper end portion;
said upper end portion being tapered outward from said neck portion upwardly to a top end of said cylindrical post so that said top end is wider than said neck portion to define one part of said interlock means which prevents the axial lift-off of said dental core, said dental core aperture being matingly tapered; and
a radially projecting key longitudinally extending along said tapered upper end portion for being received in a mating keyway provided in said dental core in communication with said dental core aperture to define another part of said interlock means which prevents the rotational displacement of said dental core.

30. A dental post system as in claim 29, wherein said lowering anchoring portion includes a plurality of externally spaced apart helical flutes longitudinally disposed about the longitudinal axis of said post for retaining said lower anchoring portion within the cement prepared bore and also for providing a vent for said post when being inserted into the cement prepared bore.

31. A dental post system as in claim 29, and further comprising a pre-formed plastic core including an embedded mating pattern for engaging with said interlock means, said plastic core being mounted onto the tooth stub to obtain a core pattern for casting said dental core, a central bore being provided in said pre-formed plastic core, said central bore being matingly tapered to receive said tapered upper end portion of said post, and a mating keyway provided in said pre-formed plastic core in communication with said central bore to receive said radially projecting key disposed on said tapered upper end portion of said post.

32. A method of restoring devitalized dentition, comprising the steps of:
preparing a tooth stub for receiving a dental post whose lower portion is to be permanently cemented into the tooth stub with its upper end portion projecting upwardly from the tooth stub;
disposing interlock means on the upper end portion for the permanent securement of a metallic core onto the dental post;
forming a core pattern on the tooth stub with the upper end portion and the interlock means disposed in the core pattern, and with the upper end portion and interlock means having mating portions within the core pattern;
releasing the interlock means and removing the core pattern from the upper end portion;
casting a metallic core from the core pattern;
interlocking the metallic core onto the upper end portion of the dental post using said interlock means so that the metallic core is secured on the tooth stub; and
fabricating a restoration upon the metallic core after the metallic core is secured on the tooth stub.

33. A method as in claim 32, and further comprising the step of cementing the lower portion of the dental post into the tooth stub prior to forming the core pattern.

34. A method as in claim 32, wherein said step of forming the core pattern comprises:
interlocking a pre-formed plastic core onto the upper end portion of the dental post using said interlock means; and
contouring the pre-formed plastic core as needed to form the desired core pattern.

35. A method as in claim 34, wherein said step of forming the core pattern further comprises the placing of a wax material between said plastic core and the tooth stub.

36. A method as in claim 32, wherein the interlock means includes a substantially U-shaped clip; and comprising:
placing the U-shaped clip to straddle the upper end portion of the dental post with the thickness of the legs of the clip being partially received in a pair of grooves provided in opposing sides of the upper end portion and the rest of the thickness of the legs being received within the formed core pattern;
removing the clip to remove the formed core pattern from the tooth stub;
seating the cast metallic core onto the upper end portion;
reinserting the clip back into composite grooves defined between the groove portions cast into the metallic core and the groove portions in the upper end portion so as to lock the metallic core to the dental post for securement on the tooth stub; and cutting off any free end portions of the legs of the clip extending beyond the periphery of the metallic core.

37. A method as in claim 32, wherein the interlock means includes an elongated cross pin; and comprising:

placing the elongated cross pin into an aperture formed in the upper end portion with a portion of the cross pin being received within the formed core pattern;

removing the cross pin to remove the formed core pattern from the tooth stub;

seating the cast metallic core onto the upper end portion; and reinserting the cross pin back into a coaxial aperture defined between an aperture cast into the metallic core and the aperture in the upper end portion so as to lock the metallic core to the dental post for securement on the tooth stub.

38. A method as in claim 37, wherein the cross pin is inserted entirely through the metallic core.

39. A method as in claim 37, wherein the cross pin is inserted through one side of the metallic core and partially into the upper end portion.

40. A method as in claim 32, wherein said step of forming the core pattern includes using impression material to build up the core pattern directly onto the upper end portion when the dental post is disposed in the tooth stub.

41. A method as in claim 32, including providing the dental post with a laterally extending shoulder portion between the upper end portion and lower portion, and providing the metallic core with a mating shoulder portion for preventing the insertion of the lower end portion into the metallic core.

42. A method as in claim 32, wherein said preparing step comprises drilling into the tooth stub to form an elongated bore; and including the steps of introducing a cement into the bore, and securing the lower portion of the dental post into the bore.

* * * * *